(12) United States Patent
Anderson et al.

(10) Patent No.: US 11,813,099 B2
(45) Date of Patent: Nov. 14, 2023

(54) DIAGNOSTIC AND IMAGING DIRECTION BASED ON ANATOMICAL AND/OR PHYSIOLOGICAL PARAMETERS

(71) Applicant: PHILIPS IMAGE GUIDED THERAPY CORPORATION, San Diego, CA (US)

(72) Inventors: David Anderson, Temecula, CA (US); Fergus Merritt, Escondido, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 506 days.

(21) Appl. No.: 17/001,329

(22) Filed: Aug. 24, 2020

(65) Prior Publication Data

US 2020/0390411 A1    Dec. 17, 2020

Related U.S. Application Data

(63) Continuation of application No. 14/961,627, filed on Dec. 7, 2015, now Pat. No. 10,751,015.
(Continued)

(51) Int. Cl.
*A61B 6/00*    (2006.01)
*A61B 8/08*    (2006.01)
(Continued)

(52) U.S. Cl.
CPC .......... *A61B 6/469* (2013.01); *A61B 5/02007* (2013.01); *A61B 5/02158* (2013.01); *A61B 6/032* (2013.01); *A61B 6/4417* (2013.01); *A61B 6/461* (2013.01); *A61B 6/504* (2013.01); *A61B 6/5217* (2013.01); *A61B 6/5247* (2013.01); *A61B 8/04* (2013.01); *A61B 8/06* (2013.01); *A61B 8/0891* (2013.01); *A61B 34/10* (2016.02); *G16H 50/30* (2018.01); *A61B 5/6852* (2013.01);
(Continued)

(58) Field of Classification Search
CPC ................................. A61B 5/02007
See application file for complete search history.

(56) References Cited

U.S. PATENT DOCUMENTS 6,930,014 B2    8/2005  Kim
8,494,794 B2    7/2013  Dutta
(Continued)

FOREIGN PATENT DOCUMENTS

| WO | 2012093260 A1 | 7/2012 |
| WO | 2012093266 A1 | 7/2012 |
| WO | 2013028612 A1 | 2/2013 |

*Primary Examiner* — Joseph M Santos Rodriguez

(57) ABSTRACT

Devices, systems, and methods of evaluating risk associated with a condition of the vessel and issuing an automatic recommendation based on co-registered physiological measurements are disclosed. The includes steps of obtaining image data for the vessel of the patient, obtaining physiological measurements for the vessel of the patient, co-registering the obtained physiological measurements with the obtained image data such that the physiological measurements are associated with corresponding portions of the vessel of the patient, analyzing the co-registered physiology measurements to identify a region of interest, and outputting, to a user interface, a suggested diagnostic procedure for the region of interest based on the analysis of the co-registered physiology measurements.

16 Claims, 11 Drawing Sheets

Related U.S. Application Data

(60) Provisional application No. 62/089,080, filed on Dec. 8, 2014.

(51) Int. Cl.

| | | |
|---|---|---|
| *A61B 6/03* | (2006.01) |
| *A61B 8/06* | (2006.01) |
| *A61B 8/04* | (2006.01) |
| *G16H 50/30* | (2018.01) |
| *A61B 5/02* | (2006.01) |
| *A61B 34/10* | (2016.01) |
| *A61B 5/0215* | (2006.01) |
| *G16H 50/20* | (2018.01) |
| *A61B 5/00* | (2006.01) |
| *A61B 90/00* | (2016.01) |

(52) U.S. Cl.
CPC . *A61B 2034/101* (2016.02); *A61B 2090/3735* (2016.02); *G16H 50/20* (2018.01)

(56) References Cited

U.S. PATENT DOCUMENTS

| | | | |
|---|---|---|---|
| 8,984,248 B2 | 3/2015 | Morishita | |
| 9,339,348 B2 | 5/2016 | Davies | |
| 2004/0122709 A1* | 6/2004 | Avinash | G16H 40/67 706/45 |
| 2006/0064396 A1 | 3/2006 | Wei | |
| 2006/0241465 A1* | 10/2006 | Huennekens | A61B 6/5247 600/458 |
| 2007/0123771 A1* | 5/2007 | Redel | A61B 6/466 600/407 |
| 2012/0053918 A1 | 3/2012 | Taylor | |
| 2014/0039276 A1 | 2/2014 | Hattangadi | |
| 2014/0114618 A1 | 4/2014 | Fonte | |
| 2014/0121513 A1 | 5/2014 | Tolkowsky | |
| 2014/0180124 A1 | 6/2014 | Whiseant | |
| 2014/0181716 A1 | 6/2014 | Merritt | |
| 2014/0187920 A1 | 7/2014 | Millett | |
| 2015/0024398 A1 | 1/2015 | Davies | |
| 2015/0025330 A1 | 1/2015 | Davies | |
| 2015/0092999 A1 | 4/2015 | Schmitt | |
| 2015/0161790 A1 | 6/2015 | Takahashi | |
| 2015/0262357 A1 | 9/2015 | Igarashi | |
| 2015/0265222 A1 | 9/2015 | Sakaguchi | |

\* cited by examiner

DIAGNOSTIC AND IMAGING DIRECTION BASED ON ANATOMICAL AND/OR PHYSIOLOGICAL PARAMETERS

CROSS REFERENCE TO RELATED APPLICATIONS

The present application is a continuation of U.S. patent application Ser. No. 14/961,627, filed Dec. 7, 2015, now U.S. Pat. No. 10,751,015, which claims priority to and the benefit of the U.S. Provisional Patent Application No. 62/089,080, filed Dec. 8, 2015, both of which are hereby incorporated by reference in their entireties.

TECHNICAL FIELD

The present disclosure relates generally to the assessment of vessels and, in particular, the assessment of the severity of a blockage or other restriction to the flow of fluid through a vessel and the treatment thereof. Aspects of the present disclosure are particularly suited for evaluation of biological vessels in some instances. For example, some particular embodiments of the present disclosure are specifically configured for the evaluation of human blood vessels.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include percutaneous coronary intervention (PCI or angioplasty), stenting, or coronary artery bypass graft (CABG) surgery. As with all medical procedures, certain risks are associated with PCI, stenting, and CABG procedures.

The severity of a stenosis is sometimes observed visually and roughly estimated based on experience. For example, a patient's vasculature can be visualized using angiography. However, even with experience and expertise, the locations of stenoses in a vessel can be difficult to visualize in a grayscale angiographic image. The use of pressure data can improve the interpretation of information gleaned from an angiogram. Moreover, the severity of stenosis can also be better understood when efficiently visualized in relation to an angiographic image in connection with such data. Further, a more complete diagnosis of the patient can be made with intravascular imaging, such as intravascular ultrasound (IVUS) or optical coherence tomography (OCT). For example, in some instances intravascular imaging can be utilized to provide a cross-sectional image of the vessel and/or characterize the type(s) of tissue/plaque present.

In order for a surgeon to make a better-informed decision regarding treatment options, additional information about the characteristics of the vessel is desirable. However, medical personnel must balance the desire for additional information with the costs (e.g., money, time, resources, risks to the patient, etc.) of obtaining the additional information.

Accordingly, there remains a need for improved devices, systems, and methods for assessing the severity of a blockage in a vessel and, in particular, a stenosis in a blood vessel. Moreover, there remains a need for improved devices, systems, and methods that prompt a user to take particular action(s) to improve the diagnosis of a patient and, thereby, improve patient treatment outcomes.

SUMMARY

Embodiments of the present disclosure are directed to providing an objective recommendation based on co-registered physiological data. One general aspect includes a method of evaluating a vessel of a patient, the method comprising: obtaining image data for the vessel of the patient; obtaining physiological measurements for the vessel of the patient; co-registering the obtained physiological measurements with the obtained image data such that the physiological measurements are associated with corresponding portions of the vessel of the patient; analyzing the co-registered physiology measurements to identify a region of interest; and outputting, to a user interface, a suggested diagnostic procedure for the region of interest based on the analysis of the co-registered physiology measurements.

In one embodiment, the obtained physiological measurements include pressure measurements, including a pressure ratio. In an aspect, the suggested diagnostic procedure includes an intravascular imaging procedure. The suggested intravascular imaging procedure may include at least one of an intravascular ultrasound (IVUS) procedure and an optical coherence tomography (OCT) procedure. The suggested diagnostic procedure may also include an intravascular flow measurement procedure. In an aspect, the obtained physiological measurements include flow measurements. In one embodiment, the suggested diagnostic procedure includes at least one of an intravascular imaging procedure and an intravascular pressure measurement procedure. The obtained image data may include image data received from an extravascular imaging system, which may include at least one of a two-dimensional angiographic image, a three-dimensional angiographic image, or a computed tomography angiographic (CTA) image.

A system for evaluating a vessel of a patient is also provided, the system comprising: a processing system in communication with at least one intravascular device, the processing system configured to: obtain image data for the vessel of the patient; obtain physiological measurements for the vessel of the patient from the at least one intravascular device; co-register the obtained physiological measurements with the obtained image data such that the physiological measurements are associated with corresponding portions of the vessel of the patient; analyze the co-registered physiology measurements to identify a region of interest; and output, to a user interface, a suggested diagnostic procedure for the region of interest based on the analysis of the co-registered physiology measurements.

In an aspect, the at least one intravascular devices includes a pressure-sensing intravascular device and wherein the obtained physiological measurements include pressure measurements. Furthermore, the processing system may be configured to calculate a pressure ratio based on the obtained pressure measurements. The suggested diagnostic procedure may also include an intravascular imaging procedure. In one embodiment, the suggested intravascular imaging procedure includes at least one of an intravascular ultrasound (IVUS) procedure and an optical coherence tomography (OCT) procedure. The suggested diagnostic procedure may include an intravascular flow measurement procedure, or may include at least one of an intravascular imaging procedure and an intravascular pressure measurement procedure.

In one embodiment, the obtained physiological measurements include flow measurements. In an aspect, the obtained image data includes image data received from an extravascular imaging system, or may include at least one of a two-dimensional angiographic image, a three-dimensional angiographic image, or a computed tomography angiographic (CTA) image.

BRIEF DESCRIPTION OF THE DRAWINGS

Illustrative embodiments of the present disclosure will be described with reference to the accompanying drawings, of which.

Figure 1:
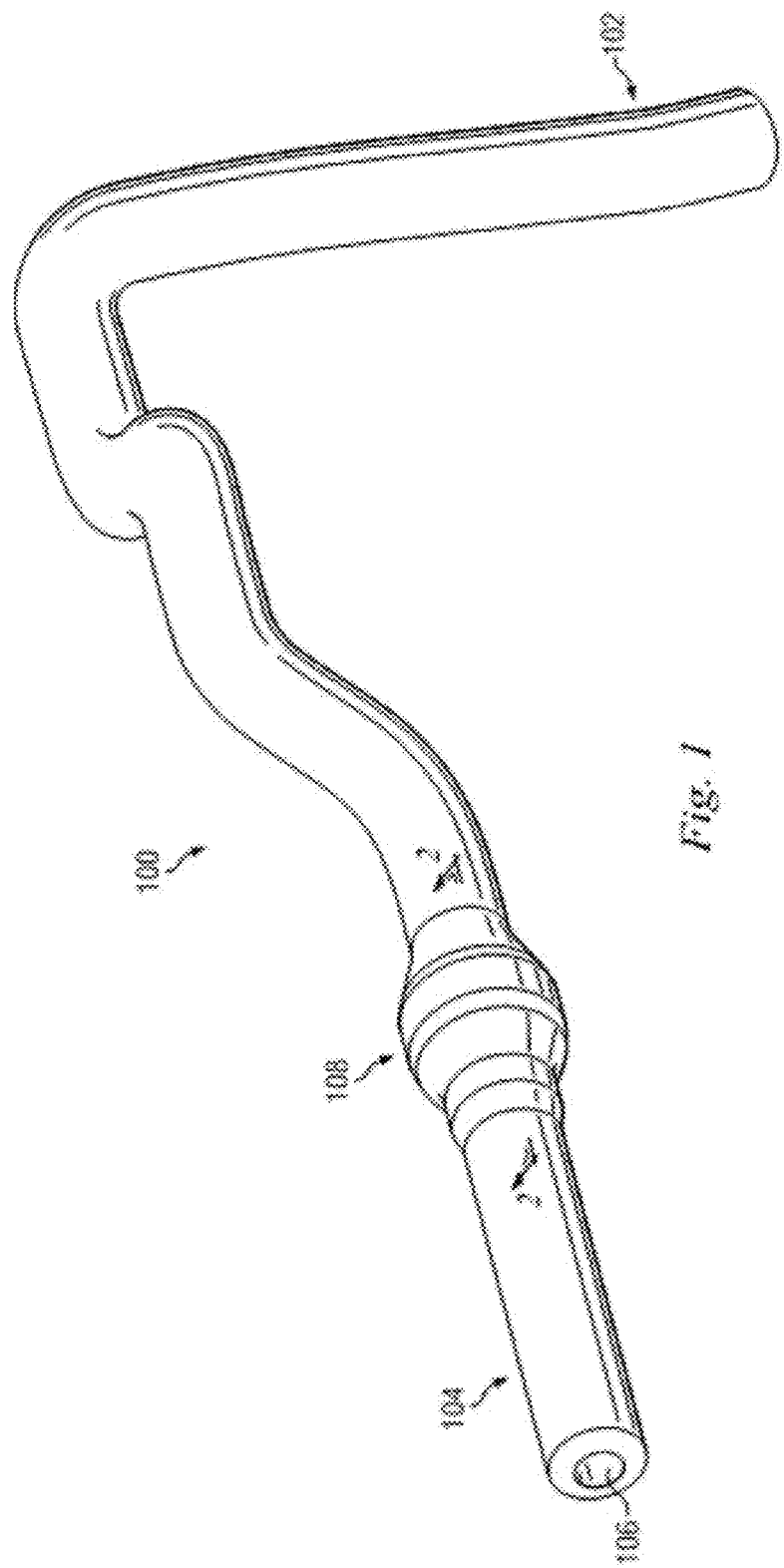
FIG. 1 is a diagrammatic perspective view of a vessel having a stenosis according to an embodiment of the present disclosure.

These drawings may be better understood by reference to the following detailed description.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Physiological measurement data and the coronary angiogram typically behave as complementary, yet segregated sources of information. The coronary angiogram has been used to make treatment decisions. More recently, physiological data (including, but not limited to, pressure and/or flow measurements, both at hyperemia and rest) have shown that better decisions can be made based on the severity of a blockage by measuring the change in underlying physiological conditions from the beginning of a target artery to the end. Treating a patient based on the severity of this change or delta has shown to improve outcomes and reduce waste from unnecessary procedures. In one or more aspects of the present disclosure, the physiological data, as collected real-time, is linked or co-registered to a schematic of the coronary arteries or an angiogram. The data may also be visually depicted in a way that allows a clinician to interact and assess where severity changes, by sliding markings as placed on the image of the vessel and correlated with the collected physiological data. One or more embodiments described herein are also able to prompt user action(s) based on the on collected physiological data. For example, additional diagnostic procedure(s) may be suggested based on potentially problematic anatomical features identified from the obtained physiological data. Additionally, embodiments may recommend performing a particular diagnostic procedure again to confirm the results of a previous medical procedure (e.g., where the obtained physiological data is at odds with expected values). Furthermore, some embodiments prompt a user to consider particular medical procedures in light of the obtained physiological data, such as a percutaneous coronary intervention (PCI) or a coronary artery bypass graft (CABG) surgery.

One aspect of the present disclosure includes superimposing real-time collected pressure and/or flow data (or other physiologic data) onto an angiogram, or a schematic of anatomy and representing the data in a way that helps a clinician determine how/where to intervene (including but not limited to CABG mapping and PCI planning). In some embodiments, the collected physiology data may include real-time data obtained during a procedure. One aspect of the present disclosure includes using the pressure, flow or other physiologic data to identify "regions of interest" where additional diagnostic information would be particularly useful for the purposes of determining how or where to intervene. Because these regions often represent potential medical issues that are best identified and/or characterized using a particular diagnostic procedure, a user can be prompted to gather further information on these regions of interest using the preferred diagnostic procedure(s). These prompts and the recommended diagnostic procedures can be presented to the clinician in a user interface showing the obtained physiological data.

Figure 2:
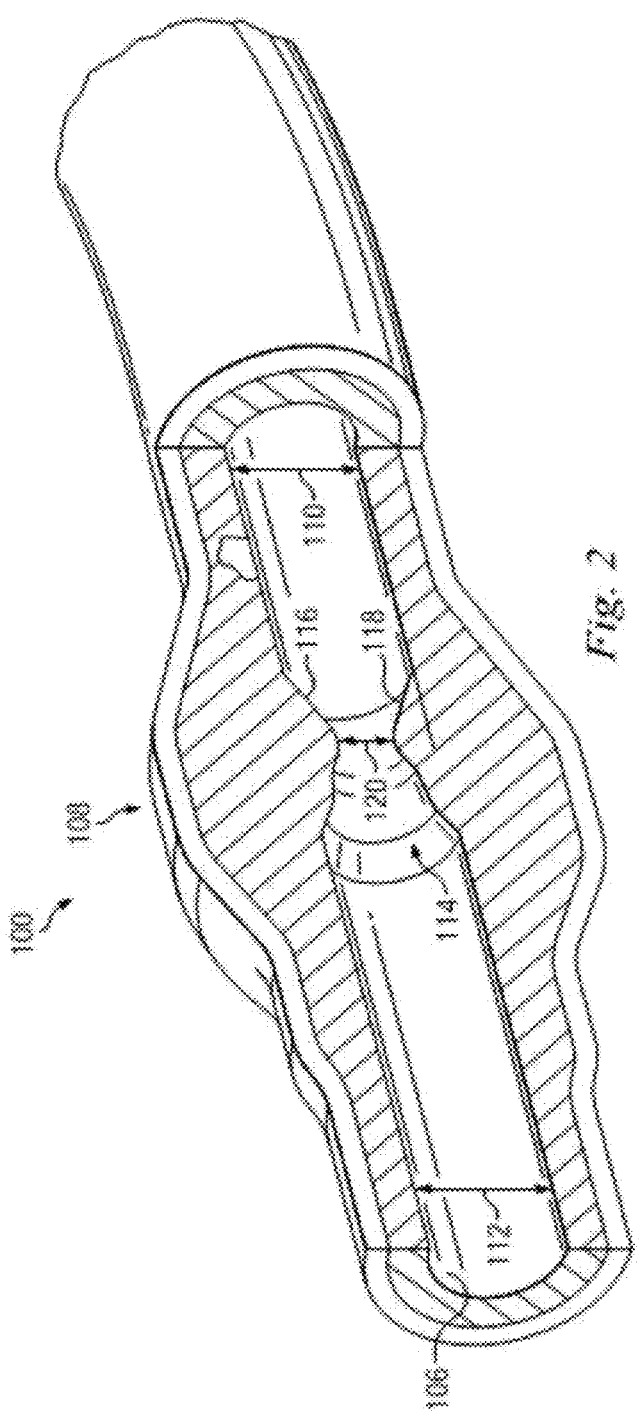
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. The stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
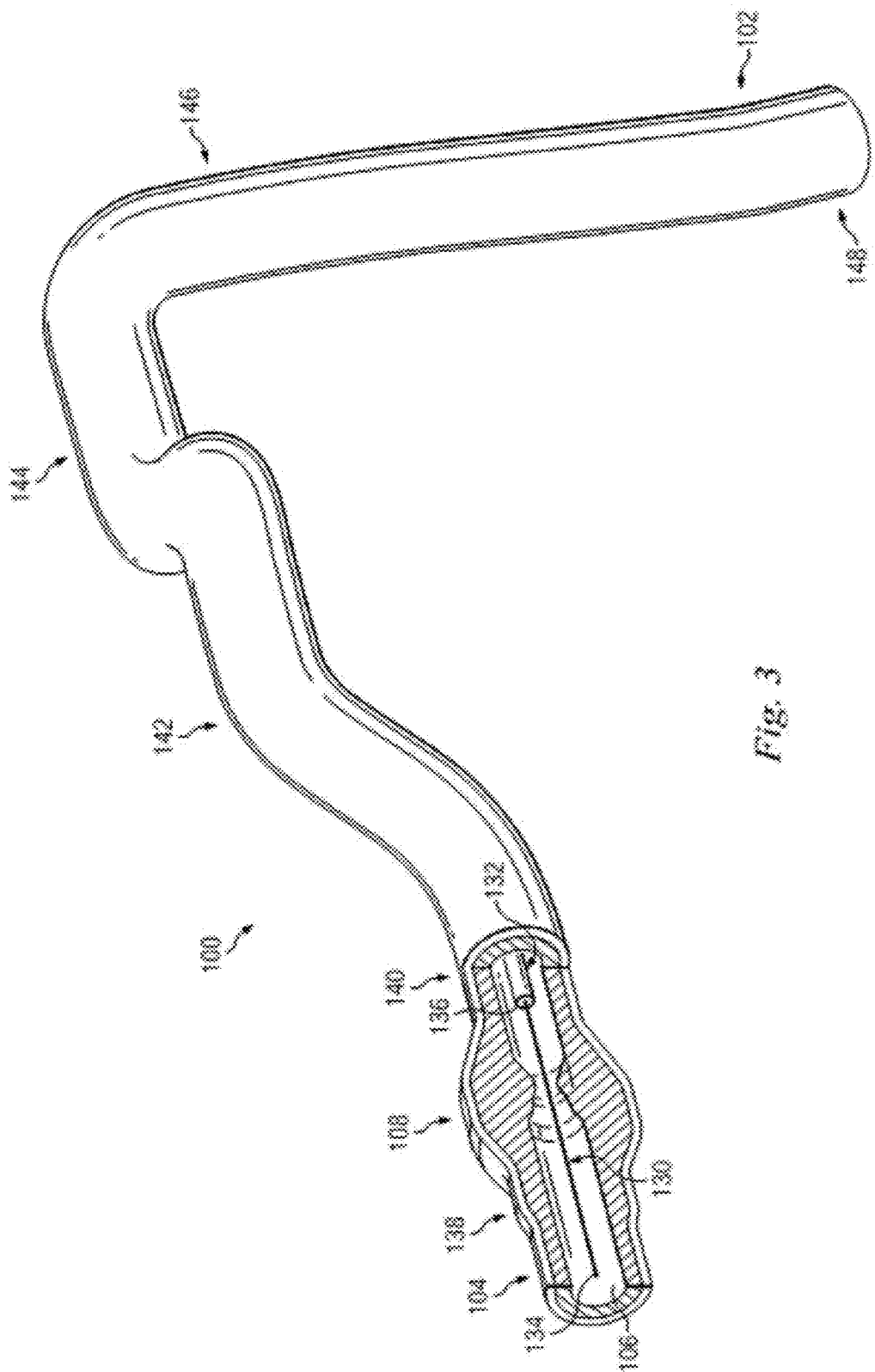
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 can include at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques.

Examples of commercially available guide wire products that include suitable pressure monitoring elements include, without limitation, the Verrata® pressure guide wire, the PrimeWire Prestige® PLUS pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less. In other embodiments, the instrument 130 has an outer diameter of 0.035" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 can also include at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Because the movement of the instrument 130 is selectable and known, the position of the distal tip 134 relative to the patient's vasculature may be estimated with sufficient precision to provide for the co-registration of data obtained by the instrument 130 with a computer model of the patient's vasculature obtained from angiography. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

In some instances, the instruments 130 and 132 may be used to provide instantaneous wave free ratio (iFR®) measurements instead of, or in addition, to traditional FFR measurements as described above. Such iFR® measurements may be obtained using products produced by the Volcano Corporation. In some embodiments, FFR data and iFR® data may be used together to assess the patient. The FFR or iFR® data may be used to determine whether the disease is focal or diffuse. In some embodiments, the pullback curve based on FFR or iFR® may be used to determine whether the patient's disease is focal or diffuse.

Figure 4:
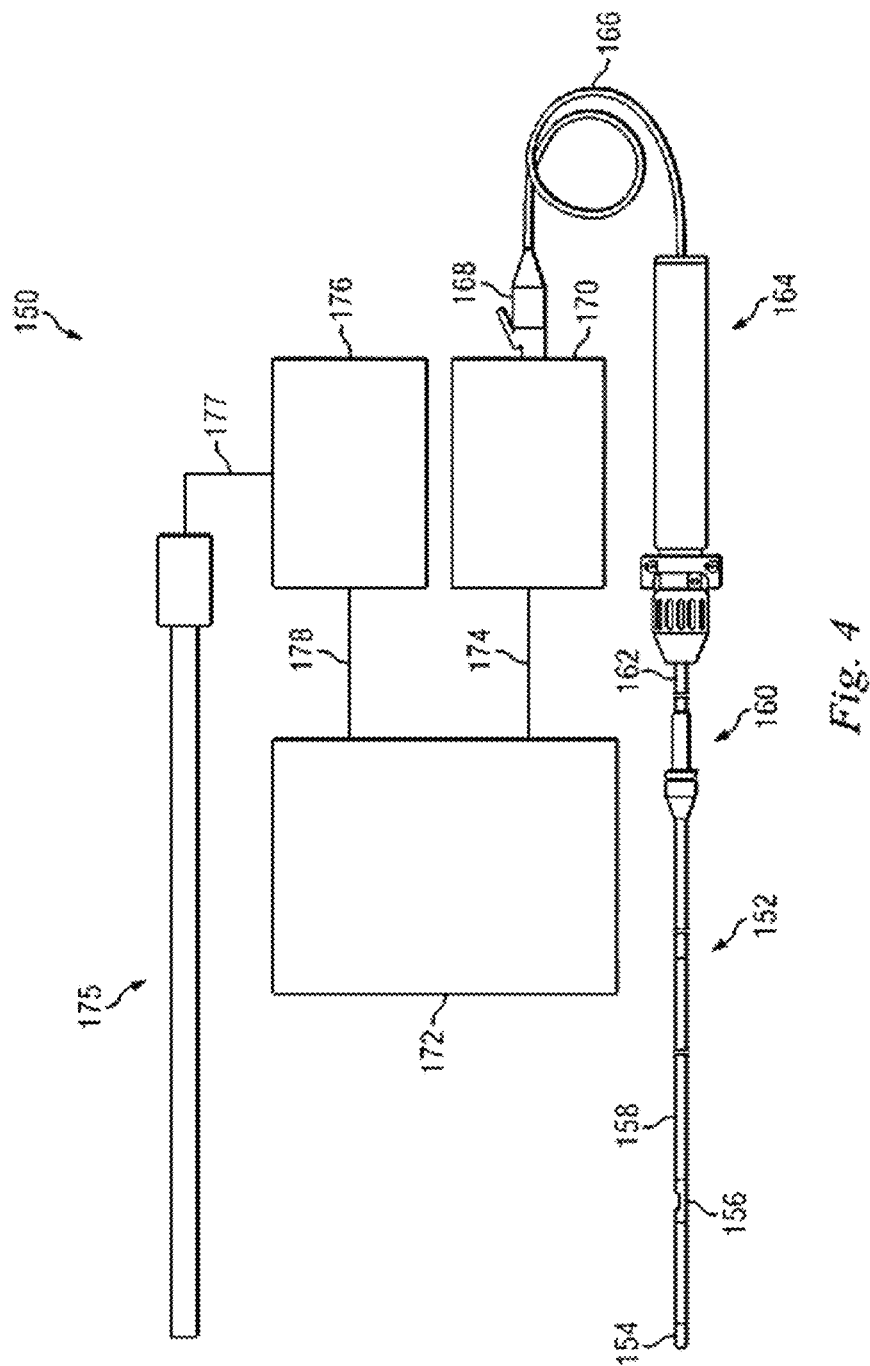
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer-readable medium accessible by the computing device. In some instances, the computing device 172 is a console device. In some particular instances, the computing device 172 is similar to the s5™ Imaging System or the s5i™ Imaging System, each available from Volcano Corporation.

In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

The computing device 172 may acquire data from many different sources. For example, as described herein the computing device 172 may communicate through the interface 170 to collect physiological measurements from instruments, such as instruments 130 and 132, positioned within a patient's vasculature. Additionally, the computing device 172 may include a network interface card or similar interface to communicate with a network 180. The computing device 172 may access angiography data to produce a model of the patient's vasculature or may access a pre-computed model. For example, an existing model of the patient's vasculature may have been generated based on previously acquired data. The computing device 172 may be coupled to a display 182 by which images, data, and user interfaces may be presented to a clinician before, after, and/or during a procedure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). For example, in some embodiments the computing device 172 may be coupled to the interface 170 by the network 180. In that regard, it is understood that the computing device 172 is positioned remote from an operating area where the instrument 152 is being used in some instances. Having the connection 174 include the connection to the network 180 can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof, and connections through the network 180. In that regard, it is understood that the connection 178 is wireless in some instances. In some instances, the connection 178 includes a communication link over a network (e.g., intranet, internet, telecommunications network, and/or other network) like the network 180. In that regard, it is understood that the computing device 172 is positioned remote from an operating area where the instrument 175 is being used in some instances. Having the connection 178 include a connection over the network 180 can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Diagnostic information within a vasculature of interest can be obtained using one or more of instruments 130, 132, 152, and 175. For example, diagnostic information is obtained for one or more coronaries arteries, peripheral arteries, cerebrovascular vessels, etc. The diagnostic information can include pressure-related values, flow-related values, etc. Pressure-related values can include distal pressure values, proximal pressure values, Pd, Pa, FFR, Pd/Pa, iFR, etc. Flow-related values can include coronary flow reserve (CFR) (e.g., maximum increase in blood flow through the coronary arteries above the normal resting volume), basal stenosis resistance index (BSR), etc.

In some embodiments, the diagnostic information can include angiographic images and/or other two-dimensional or three-dimensional depictions of a patient's vasculature. Such angiographic images may be accessed via the network 180. For example, angiographic images of the patient's vasculature and/or associated models may be stored in a data center and accessed by the computing device 172 for use during a procedure. The diagnostic information and/or data obtained by instruments 130, 132, 152, and/or 175 are correlated or co-registered to angiographic image(s) and/or other two-dimensional or three-dimensional depictions of a patient's vasculature. Co-registration can be completed using techniques disclosed in U.S. Pat. No. 6,930,014, titled "VASCULAR IMAGE CO-REGISTRATION," which is hereby incorporated by reference in its entirety, based on the known pullback speed/distance, based on a known starting point, based on a known ending point, and/or combinations thereof. In some embodiments, diagnostic information and/or data is correlated to vessel images using techniques similar to those described in U.S. patent application Ser. No. 14/144,240, titled "DEVICES, SYSTEMS, AND METHODS FOR ASSESSMENT OF VESSELS" and filed on Dec. 30, 2013, and which claims priority to U.S. Provisional Patent Application No. 61/747,480, titled "SPATIAL CORRELATION OF INTRAVASCULAR IMAGES AND PHYSIOLOGICAL FEATURES" and filed Dec. 31, 2012, which are hereby incorporated by reference in their entirety. In some embodiments, co-registration and/or correlation can be completed as described in U.S. patent application Ser. No. 14/335,603, titled "DEVICES, SYSTEMS, AND METHODS FOR ASSESSMENT OF VESSELS" and filed on Jul. 19, 2013, and which claims priority to U.S. Provisional Patent Application No. 61/856,509, titled "DEVICES, SYSTEMS, AND METHODS FOR ASSESSMENT OF VESSELS" and filed Jul. 19, 2013, which are hereby incorporated by reference in their entirety.

Figure 5:
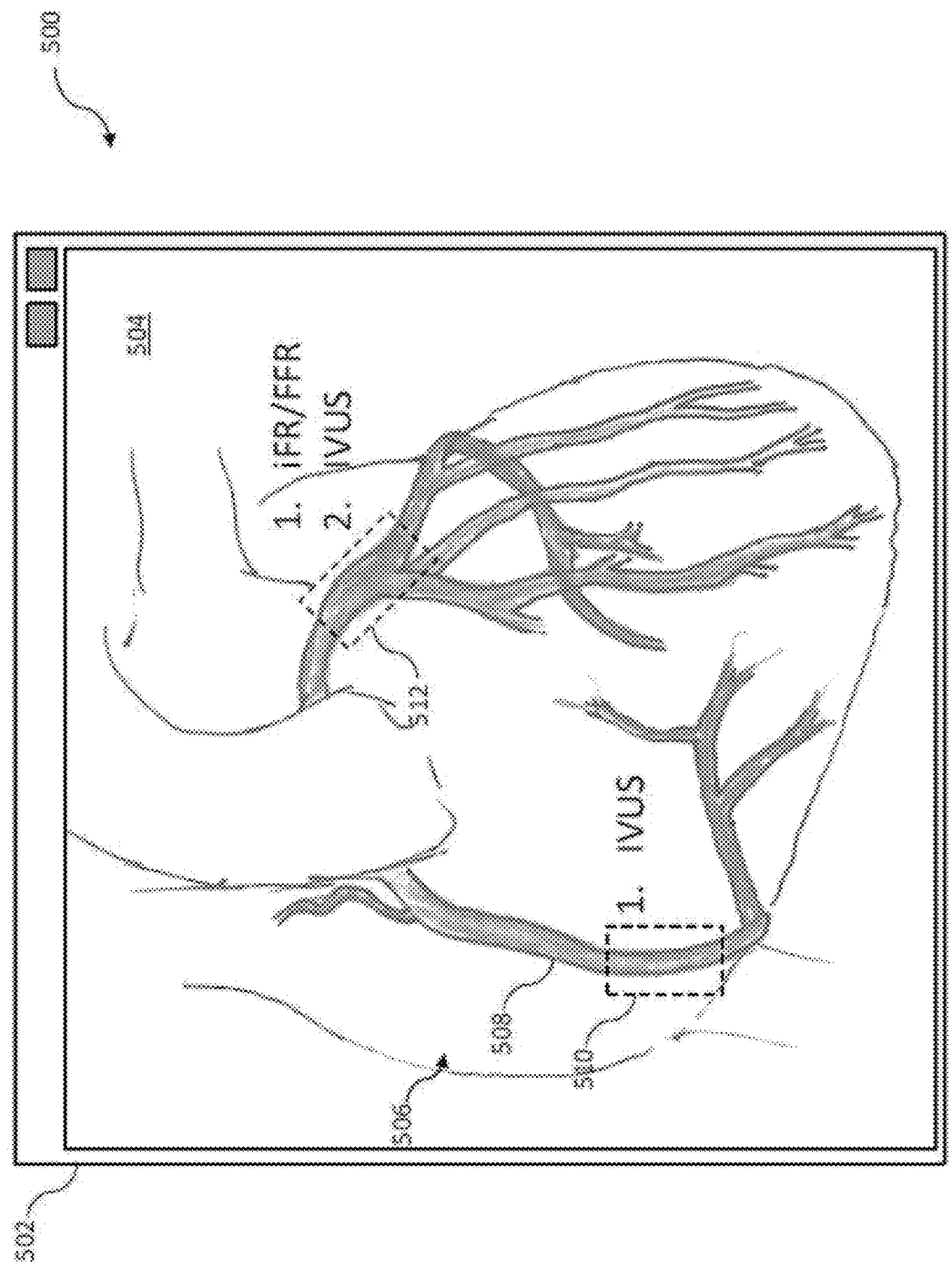
FIG. 5 is a stylized image of a patient's vasculature as seen in an angiogram image according to an embodiment of the present disclosure.

Referring now to FIG. 5, shown therein is an exemplary depiction of angiogram data as may be provided to the clinician in a user interface 500, such as may be provided by the computing device 172 of FIG. 4. The user interface 500 includes a window 502 that may be presented in the display 182 as seen in FIG. 4. The window displays angiogram data that includes cardiac tissue 506 and vasculature 508 obtained using a contrast agent. In some embodiments, the angiogram 504 may be a three-dimensional angiogram that may be manipulated by the clinician to provide different views, including different perspective views and/or cross-sectional views, of the patient's vasculature.

After obtaining the angiogram data, the data may be parsed by an image-processing component provided by the system 150 of FIG. 4 to segment the patient's vasculature and estimate certain features thereof. The parsing of the data may be performed to extract image-based physiology measurements which may be automatically displayed without the continued interaction of a clinician. For example, the image-based physiology measurements may be extracted after an angiogram collection process is complete.

When processing the angiogram data, quantitative coronary angiography (QCA) may be used to assess and identify blockages from the image-based data. A QCA process may be initiated automatically to identify any blockages. While the clinician may provide a qualitative evaluation based on his or her own experience, the information from the QCA process may be used in subsequent steps to prompt additional diagnostic procedures and/or generate an objective intervention recommendation. The image-based physiology measurements may include a dominance classification, a degree of occlusion of a lesion, which may be expressed as a percent diameter stenosis, a classification of a lesion, a degree of bending of a vessel of the vessel system, a length of a lesion, and/or a degree of calcification of a lesion.

Still referring to FIG. 5, one region of interest 510 is shown on the Left Coronary Artery while another region of interest 512 is shown on a branch of the Right Coronary Artery. These regions of interest 510, 512 may be assigned by the computing system 174 and shown on the user interface 500 based on anomalous measurements such as sharp changes in pressure readings. The user interface 500 may also display a recommendation for each region of interest as shown in FIG. 5 which may include a diagnostic procedure. For the region of interest 510 on the LCA, the user interface 500 recommends that a clinician perform an IVUS procedure on the region of interest 510. Multiple recommendations may also be displayed on the user interface 500 for problematic areas such as at region of interest 512, where the branch in the RCA could cause anomalous readings. For this region of interest 512, the user interface 500 recommends that the clinician perform an iFR or FFR procedure followed by an IVUS procedure for added certainty. These recommendations may be based on multiple modalities of physiological data including, but not limited to, pressure measurements, flow (velocity) measurements, images (including images obtained using ultrasound (e.g., IVUS), OCT, thermal measurements, (and data collected from other imaging techniques), temperature measurements, and/or combinations thereof.

During subsequent procedures, the clinician may navigate the instruments 130 and/or 132 through the patient's vasculature, collecting physiology measurements therein. The physiology measurements may be stored in a memory of the computing device 172 and also displayed on the display 182. As is discussed in further detail below, co-registration techniques incorporated herein by reference and others that may be known to those of skill in the art may be used to co-register physiology measurements to specific portions of the patient's vasculature 508.

Figure 6:
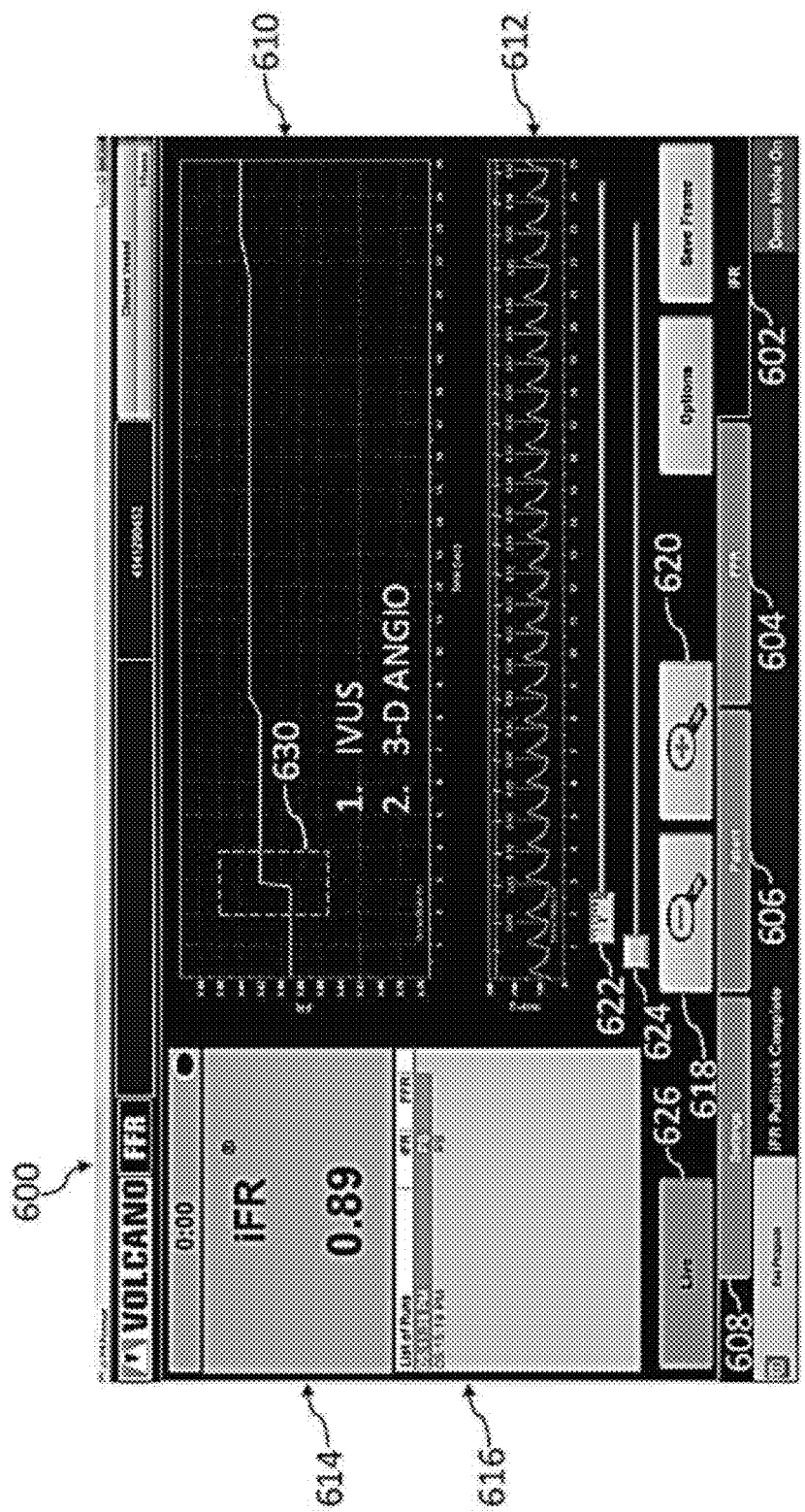
FIG. 6 is a graphical user interface screen display according to an embodiment of the present disclosure.

Referring now to FIG. 6, shown therein is a depiction of a user interface 600 for evaluating a vessel based on obtained physiology measurements (as depicted, pressure measurements, but may also include flow volume, flow velocity, and/or other intravascular physiology measurements or calculations based thereon) according to embodiments of the present disclosure. The user interface may be displayed on a touch-sensitive display. A clinician can view, analyze, and interact with the pressure data and/or visual representations of the pressure data.

Referring more specifically to FIG. 6, shown therein is a screen display 600 according to an embodiment of the present disclosure. The screen display 600 includes multiple tabs, including an iFR tab 602, an FFR tab 604, a patient tab 606, and a settings tab 608. In FIG. 6, the iFR tab 602 has been selected and displayed to a user. As shown, the iFR tab 602 includes a graph 610 and a corresponding pressure waveform plot 612. The screen display 600 also includes a window 614 that shows a calculated pressure ratio (e.g., FFR, iFR, or otherwise). The screen display 600 also includes a window 616 showing the runs or pullbacks available for display to the user. In the illustrated embodiment, two different runs are available and identified by a corresponding time stamp. In that regard, a user can select the desired run from the window 616 and the data shown in the graph 610 and pressure waveform plot 612 will update accordingly.

The screen display 600 also includes zoom buttons 618, 620 that allow a user to zoom out or in, respectively, on the graph 610 and the pressure waveform plot 612. To this end, the screen display 600 includes a ruler 622 showing the relative scale of the graph 610 and the pressure waveform plot 612. In some instances, the ruler 622 provides a dimensional scale of the graphical display of the graph 610 and/or the pressure waveform plot 612 relative to the vessel length and/or the pullback length. The scale of the ruler 622 automatically updates in response to selective actuation of the zoom buttons 618, 620 in some implementations.

The screen display 600 also includes a slider 624. The slider 624 allows the user to move along the length of the vessel and/or the corresponding pullback data. For example, in some instances the left end of the slider 624 corresponds to the beginning of the pullback and the right end of the slider corresponds to the end of the pullback. By moving the slider 624 between the first and second ends, a user can see corresponding portions of the pressure data in the graph 610 and the pressure waveform plot 612. Accordingly, a user can focus on certain portions of the vessel and pullback data using the zoom buttons 618, 620 in combination with the slider 624. In some instances, the numerical value of the pressure ratio displayed in window 614 is updated based on the position of the slider and/or. In that regard, in some instances the numerical value of the pressure ratio displayed in window 614 is based solely on the pressure data being displayed in the graph 610 and the pressure waveform plot 612. However, in other instances the numerical value of the pressure ratio displayed in window 614 is based one of or a combination of the pressure data being displayed in the graph 610 and the pressure waveform plot 612 and pressure data not displayed in the graph 610 and the pressure waveform plot 612.

In that regard, the graph 610 and pressure waveform plot 612 of screen display 600 illustrate aspects of pressure measurements obtained as one instrument is moved through the vessel and another instrument is maintained at a fixed location. In that regard, in some instances the pressure measurements are representative of a pressure ratio between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer to the fixed position of the proximal pressure measurement). For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances.

In some embodiments a diagnostic window is selected using one or more of the techniques described in U.S. patent application Ser. No. 13/460,296, filed Apr. 30, 2012 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In the illustrated embodiment of FIG. 6, the graph 610 shows the pressure ratio over time. In particular, the graph 610 shows the pressure ratio calculated over the time of a pullback. More specifically, the graph 610 shows an iFR pressure ratio value during a pullback. In that regard, the iFR pressure ratio may be calculated as described in one or more of PCT Patent Application Publication No. WO 2012/093260, filed Jan. 6, 2012 and titled "APPARATUS AND METHOD OF CHARACTERISING A NARROWING IN A FLUID FILLED TUBE," PCT Patent Application Publication No. WO 2012/093266, filed Jan. 6, 2012 and titled "APPARATUS AND METHOD OF ASSESSING A NARROWING IN A FLUID FILLED TUBE," U.S. patent application Ser. No. 13/460,296, filed Apr. 30, 2012 and titled "DEVICES, SYSTEMS, AND METHODS FOR ASSESSING A VESSEL," PCT Patent Application Publication No. WO 2013/028612, filed Aug. 20, 2012 and titled "DEVICES, SYSTEMS, AND METHODS FOR VISUALLY DEPICTING A VESSEL AND EVALUATING TREATMENT OPTIONS," U.S. Provisional Patent Application No. 61/856,509, filed Jul. 19, 2013 and titled "DEVICES, SYSTEMS, AND METHODS FOR ASSESSMENT OF VESSELS," and U.S. Provisional Patent Application No. 61/856,518, filed Jul. 19, 2013 and titled "DEVICES, SYSTEMS, AND METHODS FOR ASSESSING A VESSEL WITH AUTOMATED DRIFT CORRECTION," each of which is hereby incorporated by reference in its entirety.

The graph 610 can illustrate the pressure ratio and/or the underlying pressure measurements in any suitable way. Generally speaking, the representation of the data in graph 610 can be utilized to identify gradients/changes in the pressure ratio and/or the underlying pressure measurements that can be indicative of a significant lesion in the vessel. In that regard, the visual representation of the data can include the pressure measurement(s); a ratio of the pressure measurements; a difference in the pressure measurements; a gradient of the pressure measurement(s), the ratio of the pressure measurements, and/or the difference in the pressure measurements; first or second derivatives of the pressure measurement(s), the ratio of the pressure measurements, and/or the difference in the pressure measurements; and/or combinations thereof.

Likewise, the pressure waveform plot 612 shows the corresponding pressure data. In that regard, the pressure waveform plot 612 can include the pressure waveform for the pressure sensing device moved through the vessel during the pullback, the pressure waveform for the stationary pressure sensing device, or both. In the illustrated embodiment, the pressure waveform plot 612 includes the pressure waveforms for both. In some instances the pressure waveform plot 612 is augmented to highlight or otherwise accentuate the pressure data corresponding to the diagnostic window utilized for the pressure ratio calculations.

As shown in FIG. 6, the screen display 600 includes a button 626 indicating that the data is being displayed in a "Live" mode, which indicates that the screen display 600, including graph 610, pressure waveform plot 612, and/or the window 614, is being updated in real time as a procedure is being performed. In other instances, the button 626 of the screen display 600 will indicated that it is in "Playback" or "Review" mode, which indicates that the screen display 600 is showing data obtained previously. With respect to the "Live" mode, it should be noted that the determination of the diagnostic window and/or the calculation of the pressure differential are performed in approximately real time or live to identify the diagnostic window of the heartbeat cycle and calculate the pressure differential. In that regard, calculating the pressure differential in "real time" or "live" within the context of the present disclosure is understood to encompass calculations that occur within 10 seconds of data acquisition.

It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

Also shown on FIG. 6 is region of interest 630. The region of interest 630 may be assigned by the system 150 based on anomalous readings from the instruments such as drastic pressure changes in the vessel. In this embodiment, the region of interest 630 is centered around a sharp pressure change in the vessel. When such an region of interest 630 is identified by the system 150, the screen display 600 may show one or more options for taking further diagnostic measurements of the region of interest 630. Therefore, the screen display 600 shown in FIG. 6 prompts a medical professional to perform an IVUS measurement on the identified section of the vessel which may be further confirmed by a three-dimensional angiogram.

The coloring and/or other visually distinguishing aspect of the pressure differential measurements depicted in graph 610 and/or window 614 of the screen display 600 of FIG. 6 are configured based on the threshold value in some instances. For example, a first color (e.g., green, white, or otherwise) can be utilized to represent values well above the threshold value (e.g., where the threshold value is 0.80 on a scale of 0.00 to 1.00, values above 0.90), a second color (e.g., yellow, gray, or otherwise) can be utilized to represent values near but above the threshold value (e.g., where the threshold value is 0.80 on a scale of 0.00 to 1.00, values between 0.81 and 0.90), and a third color (e.g., red, black, or otherwise) can be utilized to represent values equal to or below the threshold value (e.g., where the threshold value is 0.80 on a scale of 0.00 to 1.00, values of 0.80 and below). Further, in some instances the graph 610 includes one or more horizontal lines or other depictions representing the threshold value(s). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

Figure 7:
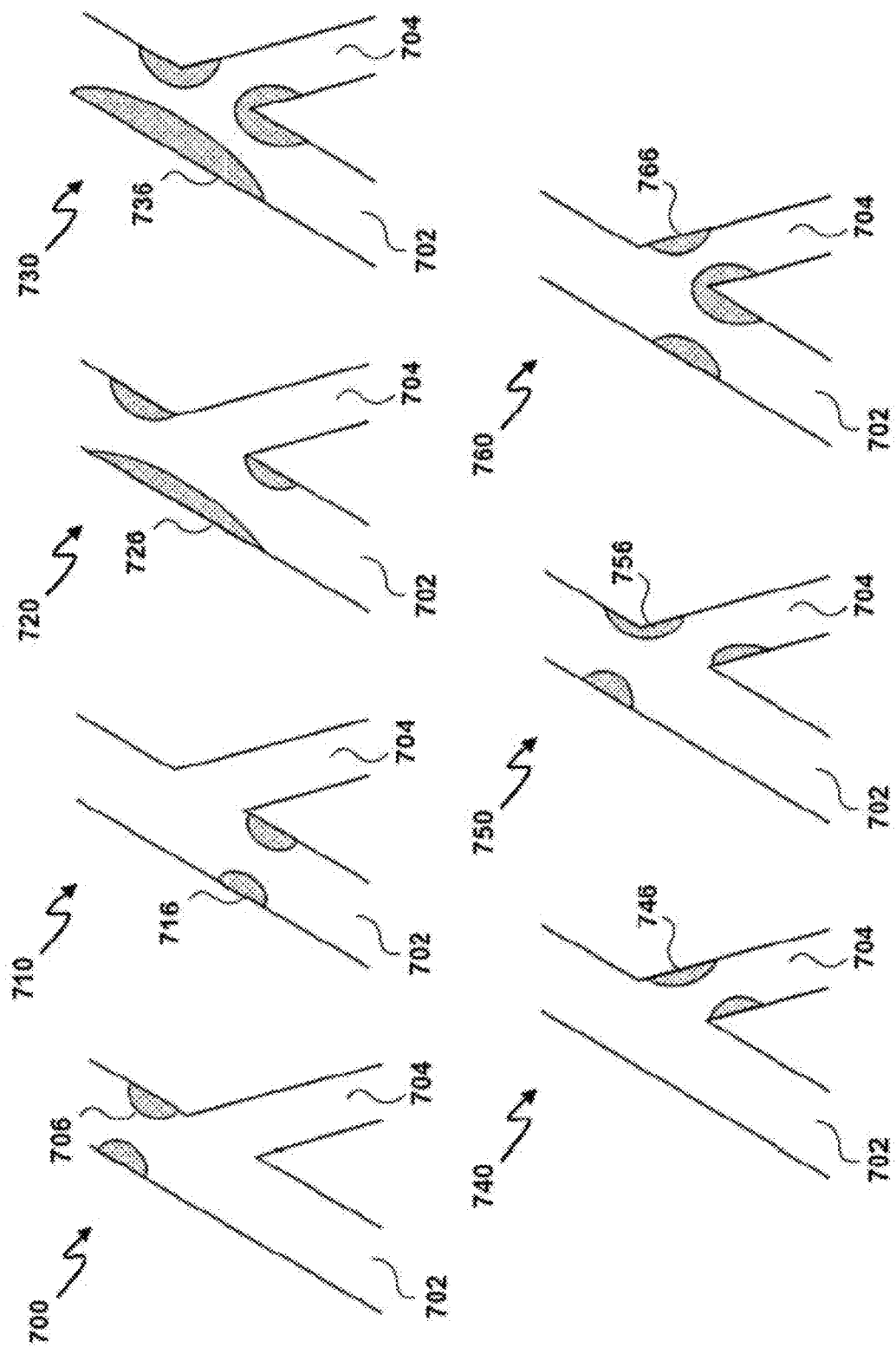
FIG. 7 is a series of stylized images of a vessel illustrating classification of vessel obstructions according to an embodiment of the present disclosure.

Referring now to FIG. 7, shown therein is a plurality of bifurcation lesions that may be detected and classified using imaging data, such as may be provided by IVUS inspection. The bifurcations lesions shown are examples of situations where IVUS may be particularly useful in diagnosing vessels and determining appropriate treatment options. As previously shown in FIG. 5, IVUS may be used in conjunction with other diagnostic procedures to resolve anomalous measurements and provide accurate data. Furthermore, the bifurcation lesions discussed in conjunction with FIG. 7 will be referred to in FIG. 9. The imaging data may include an indication of whether an imaged surface is tissue or plaque, such as a calcium deposit. The bifurcation 700 includes a main vessel 702 and a side vessel 704, and includes a stenosis 706 within the main vessel 702 only and positioned before the branching of the side vessel 704. The bifurcation 710 depicts a stenosis 716 positioned within the main vessel 702 only and after the branching of the side vessel 704. Bifurcation 720 includes a stenosis 726 situated adjacent to the branching of the side vessel 704, but limited to the main vessel 702. The stenosis 726 includes portions both before and after the branching of the side vessel 704 the bifurcation 730 includes a stenosis 736 that is situated adjacent to the branching of the side vessel 704, similar to the stenosis 726. However, the stenosis 736 includes portions within the side vessel 704. The bifurcation 740 includes a stenosis 746 situated within the side vessel 704 only. The bifurcation 750 includes a stenosis 756 adjacent to the branching and including a portion before the branching in the main vessel 702 and a portion after the branching in the side vessel 704. The bifurcation 760 depicts a stenosis 766 having portions proximate the branching and after the branching in both the main vessel 702 and the side vessel 704. Using IVUS data or other suitable data, the system 150 may perform image-processing and image-recognition to classify lesions occurring in each of the segments of interests. The segments may be labeled with the conventional names for each of the segments. Information regarding the segments, including classifications and associated severities, may be provided to a computing device 172.

Figure 8:
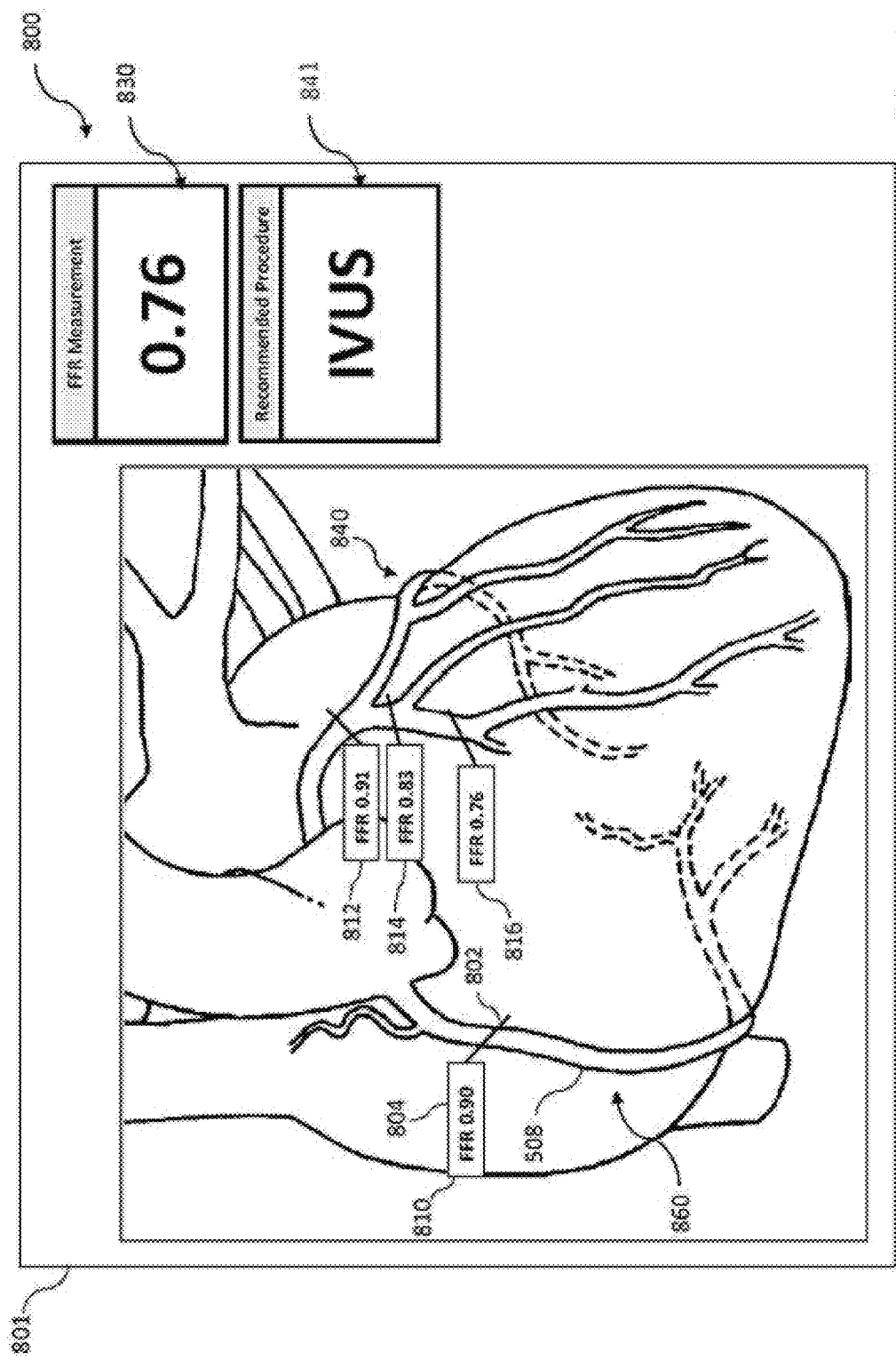
FIG. 8 is a stylized image of a patient's vasculature as seen in a user interface according to an embodiment of the present disclosure.

Referring now to FIG. 8, shown therein is an annotated depiction of stylized images of a vessel according to embodiments of the present disclosure. The stylized user interface 800 of FIG. 8 may be presented to a clinician in a display, as a window 801, and incorporates angiogram data with an overlay of co-registered physiology measurements as described herein. As described herein, multiple types of data may be used by the system to formulate and recommend diagnostic procedures to a clinician. For example, physiology measurements collected using pressure sensors or other sensors may be co-registered with the angiogram data or, in some embodiments, with a two-dimensional or three-dimensional model prepared therefrom. In other embodiments, angiogram data and the co-registered physiology measurements may be presented separately and not overlaid as illustrated. FIG. 8 includes stylized images 840 and 860 of the right coronary artery and of the left coronary artery, respectively. FIG. 8 can be displayed on a display 182 of system 150 for assessing a patient's vasculature. That is, one or more components (e.g., a processor and/or processing circuit) of the system can render information, including angiogram data and physiology measurements, to provide display data to cause the display of the images shown in FIG. 8. In some embodiments, the representations of the LCA 860 and the RCA 840 may be further stylized and/or presented without the underlying angiogram data.

The images of the stylized vessels in FIG. 8 are annotated with one or more visualizations configured to assist in identifying one or more lesions and/or stenoses, and/or assess the severity thereof. These annotations may be automatically provided by performing image-recognition on angiogram data and/or other data, such as IVUS imaging data. The visualizations are based on physiology values obtained from one or more instruments (e.g., instruments 130 and/or 132) as at least one of the instruments is moved through the vessel. The stylized vessels of FIG. 8 can be colorized and/or otherwise visualized using a heat map that illustrates changes in pressure measurements (or other physiology measurements, such as flow volume, flow velocity, calcium deposits, etc.) obtained as the instrument is moved through the vessel. In some instances a proximal pressure measurement is obtained at a fixed location within the vessel while the instrument is pulled back through the vessel from a first position distal of the position where the proximal pressure measurement is obtained to a second position more proximal than the first position (i.e., closer the fixed position of the distal pressure measurement), such as is discussed herein in connection with FIG. 6. Accordingly, FIG. 8 includes depictions of co-registered physiology measurements.

By comparing the calculated pressure differential to a threshold or predetermined value, a clinician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

Markers 802 show pressure readings of specific sections of the vessel and can be described as tick marks. In some embodiments, markers 802 can extend transversely across the vessel. In other embodiments, markers 802 can take different shapes (e.g., circles, squares, etc.), be in different positions relative to the vessel (beside, within, etc.), be differently sized, etc. The markers and corresponding measurements can be utilized to both identify the location of the lesion or stenosis within the vessel and assess the severity of the lesion or stenosis. For example, under some conditions, the angiogram data may appear to show a normal vessel, while the physiology measurements presented on the user interface 800 (and shown overlaid on the angiogram data) may provide additional information.

FIG. 8 includes visualizations for providing diagnostic information collected by one or more instruments at a corresponding location of the vessel on the display. In that regard, value indicators 804 can be disposed adjacent to markers 802 to indicate the location within the patient's vasculature to which the measurement corresponds. In other embodiments, value indicators 804 are displayed further away from markers 802, but an additional visual element (e.g., an arrow, a straight line, a curved line, marker 802 and value indicator 804 are the same or similar colors, etc.) is provided to indicate the location of the measurement. In some embodiments, the value indicators 804 include only the value of the physiological measurement (e.g., "0.90"), while in other embodiments, the value indicators 804 include the value and type of physiological measurement (e.g., "0.90 FFR"). In the example of FIG. 8, value indicators 810, 812, 814, 816 show various FFR values in the vessels. One of the value indicators 816 may be selected by the clinician and the corresponding measurement is displayed in window 830. In yet other embodiments, additional information, such as the time the measurement was taken, severity of the stenosis or lesion, etc. can also be provided by the value indicators 804. For example, a user may provide a user input (e.g., a selection from a drop-down menu, toggle through the available options, etc.) selecting the types of information that should be displayed in value indicators 804.

In some embodiments, markers 802 and/or value indicator 804 can be positioned automatically based on the physiology measurements. The system can be configured to select locations within the vessel that are clinically significant based on the diagnostic information (e.g., locations where the physiology measurements change significantly, such as points at which pressure changes). Similarly, the one or more visualizations of FIG. 8 can include markers 802 and/or value indicator 804 for various predefined segments of the patient's vasculature. The segments identified by value indicators 804 include, but are not limited to, right coronary artery (RCA), left main coronary artery, circumflex coronary artery, left anterior descending (LAD), RCA proximal, RCA mid, RCA distal, LAD proximal, LAD mid, LAD apical, first diagonal, additional first diagonal, second diagonal, additional second diagonal, proximal circumflex, intermediate/anterolateral, obtuse marginal, distal circumflex, left posterolateral, posterior descending, among others. These value indicators 804 may also be automatically generated based on the angiogram data using image-recognition and modeling techniques. Labels 804 can be textual indications providing the names of major and/or minor vessels or segments thereof and can include alphabetical, numeric, and/or other symbolic characters. In some embodiments, the value indicators 804 are included automatically by the system 150 upon performing an image-recognition process on the angiogram information such as that depicted in the user interface 500 of FIG. 5. The angiogram information may include, information characterizing or describing features of the vessel system such as the contours, location, branches, and other features of the vessel(s) to automatically identify individual vessels within the patient's vasculature. In this way, a model of the patient's vasculature may be generated and parsed to identify specific sections warranting the appropriate label. While abbreviations and particular vessels are used in FIG. 8, it is understood that any suitable label can be used.

The co-registered physiology measurements may be used to ensure the accuracy of prompts. For example, when the physiology measurements indicate that a lesion automatically detected from the angiogram data causes an insignificant pressure drop within the vasculature, a factor may attached in the analysis of the system 150 to appropriately weigh the severity of the corresponding lesion. While the visual data may provide sufficient information to obtain a disease quantification score, the physiology data may indicate the relative significance of each identified lesion.

Markers 802 and value indicators 804 may also be used by the system to issue recommendations or prompts to a medical professional. In some embodiments, markers 802 are set in potential risk areas, such as probable locations of lesions or stenosis. These markers 802 are recorded during diagnostic sessions and may be reviewed after medical procedures have taken place. In the example shown in FIG. 8, value indicator 816 shows a reading of 0.76 which may be indicative of a stenosis. Therefore, the system 150 issues a recommended procedure prompt in window 841 to use IVUS to confirm that the stent was accurately deployed and is functioning properly.

Figure 9:
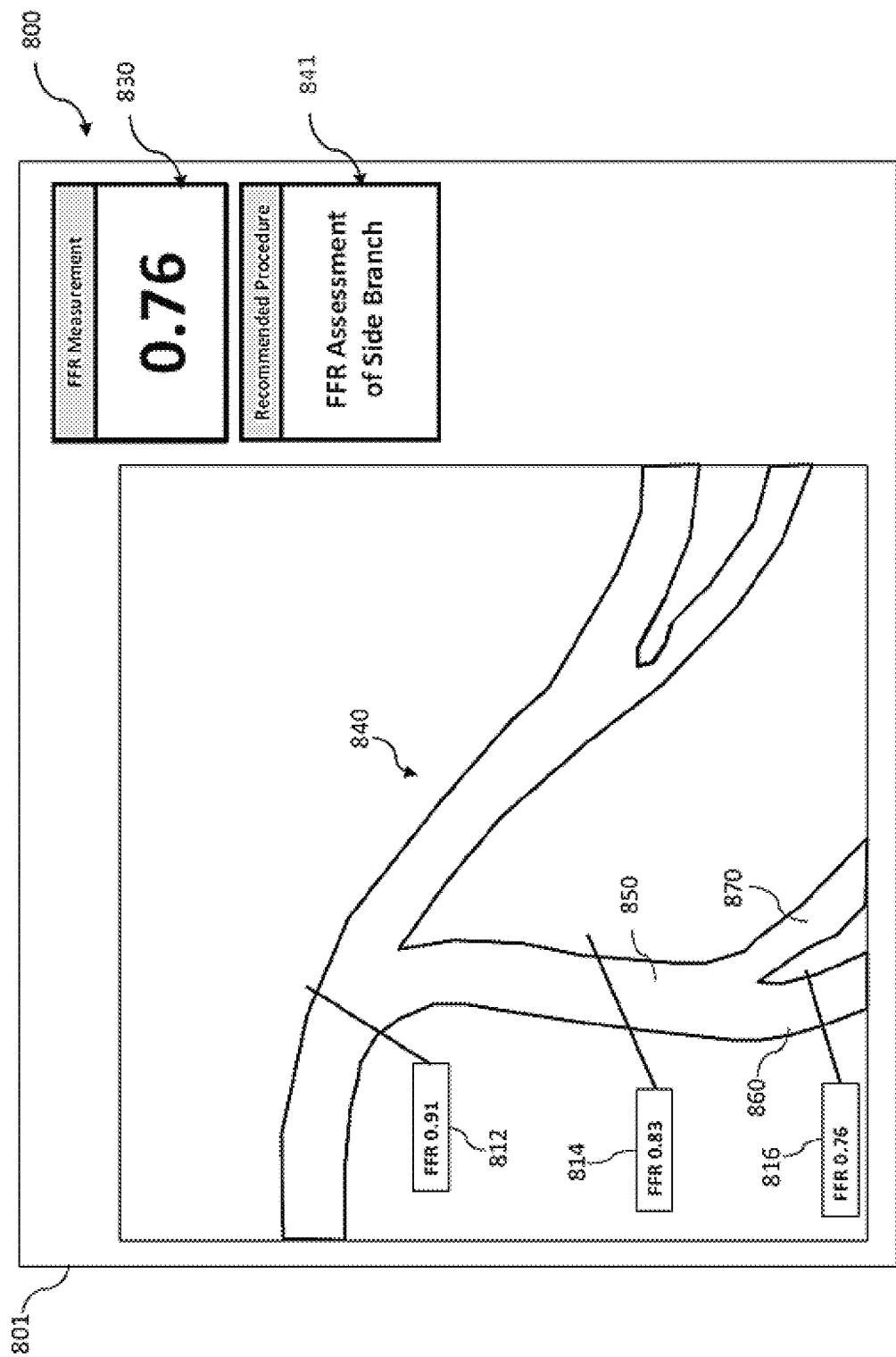
FIG. 9 is a magnified view of the stylized image of a patient's vasculature of FIG. 8 as seen in a user interface according to an embodiment of the present disclosure.

FIG. 9 shows a system 150 displaying a magnified view of the stylized RCA 840 in the user interface 800 of FIG. 8. A clinician may use the user interface to view magnified images of any section of the vessel system including a region of interest to better understand the condition of the vessel. According to one embodiment of the present disclosure, anatomy and physiology can be analyzed to direct diagnostic procedures in stenosis located at bifurcations. For example, a main vessel 850 branches into a main branch 860 and a side branch 870. FFR measurements are taken at various sites that are marked by markers and visual indicators 812, 814, 816 along the vessel. In this situation, where measurements are taken along some vessels in the vessel system, it is common for ambiguities to arise in measurements because the location of plaques in the vessel may vary widely. In particular, the distribution of plaques can vary widely around bifurcations in the vessel (see FIG. 7 for exemplary plaque distributions), which can lead to pressure anomalies. IVUS is often used to determine the location of the plaques in a bifurcation so that the lesion can be appropriately classified prior to determining the therapeutic plan. If co-registered iFR or FFR data shows a possible stenosis near a bifurcation (as seen by an FFR measurement of 0.76 for value indicator 816), then the system 150 prompts a user in window 841 to perform a pressure assessment of the side branch 860 before or after delivery of therapy. For example, a user may be prompted to perform an iFR or FFR measurement when a stent is deployed in an area known to be prone to stent under-deployment. In some instances, use of iFR or FFR on the side branch of a bifurcation can be utilized to determine whether to treat that side branch. For example, after treatment of one side of the bifurcation with a stent, ablation, or otherwise, the other side branch may look to have a significant blockage on the angio image, but iFR or FFR may show that the blockage is not physiologically significant such that there is no need to treat the side branch.

Figure 10:
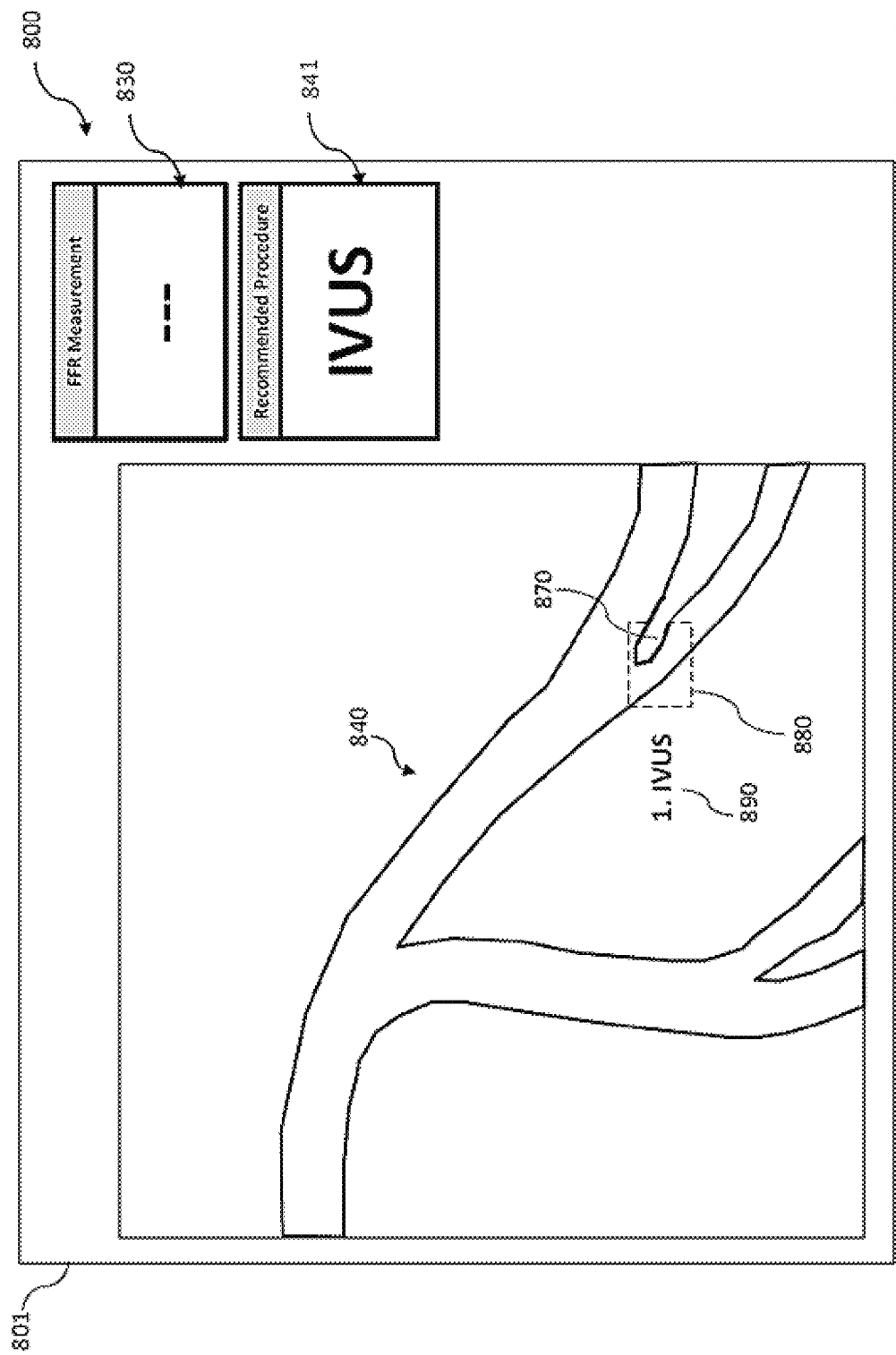
FIG. 10 is a magnified view of the stylized image of a patient's vasculature of FIG. 8 as seen in a user interface according to another embodiment of the present disclosure.

Co-registered data may also be useful in identifying anatomical features that are best resolved with a particular diagnostic modality such as intravascular imaging. The system is configured to issue a prompt to a user when indications of such features are present in the obtained physiological data. In the example of FIG. 10, the angiographic image of the vessel indicates a narrowing 870 in a vessel. The initial images of the narrowing 870 may be captured with an external imaging system such as automated quantitative coronary angiography (QCA). IVUS is particularly useful in diagnosing narrowed vessels because of the precision of the images available. Based on the QCA or other physiological data, a user may be prompted to perform intravascular imaging, such as IVUS or OCT. In this regard, the system 150 can prompt the user to perform IVUS measurements on the narrowed section 870. In some embodiments, there can be more than one prompt issued for a given data set. In this case, the system 150 highlights or otherwise marks the region of interest (e.g., with outline 880 or other suitable indicator) and issues a corresponding prompt 890 on the user interface 800 in proximity of the region of interest. Additionally, the recommended procedure is shown in window 841. In addition to IVUS, system 150 may recommend other diagnostic procedures such as 3-D angio. In any case, the use of a variety of data sources allows potentially problematic anatomic anomalies to be more easily identified and addressed.

The one or more visualizations of FIGS. 5-10 can include or be supplemented with information regarding characteristics of the lesion or stenosis and/or the vessel using one or more other vessel data-gathering modalities prompted by the system. The other representations of the lesion or stenosis and/or the vessel can include, e.g., IVUS (including virtual histology), OCT, ICE, Thermal, Infrared, flow, Doppler flow, and/or other vessel data-gathering modalities. The additional information can provide a more complete and/or accurate understanding of the vessel characteristics and/or assist in evaluating a risk associated with a lesion or stenosis. For example, in some instances the additional information can be utilized to make treatment decisions for borderline cases.

It is understood that numerous other visualization techniques may be utilized to convey the information of FIGS. 5-10 in the context of an angiographic image or other image of the vessel (including both intravascular and extravascular imaging techniques, such as IVUS, OCT, ICE, CTA, etc.) to help the user evaluate the vessel. In that regard, while the examples of the present disclosure are provided with respect to angiographic images, it is understood that the concepts are equally applicable to other types of vessel imaging techniques, including intravascular and extravascular imaging. In some instances, a user is able to select what information should be included or excluded from the displayed image. In that regard, it should be noted that these visualization techniques related to conveying the pressure measurement data in the context of an angiographic or other image of the vessel can be utilized individually and in any combinations. For example, in some implementations a user is able to select what visualization mode(s) and/or portions thereof will be utilized and the system outputs the display accordingly. Further, in some implementations the user is able to manually annotate the displayed image to include notes and/or input one or more of the measured parameters.

The images of vessels in FIG. 5-10 can include three-dimensional, two-dimensional, angiographic, a computed tomography angiographic (CTA), and/or other suitable forms of images. In some embodiments, a three-dimensional image may be rotated about a vertical axis. In some embodiments, a two-dimensional image may include multiple views about a vertical axis such that different two-dimensional views are shown when the image is rotated. In some implementations, the three dimensional model is displayed adjacent to a corresponding two dimensional depiction of the vessel. In that regard, the user may select both the type of depiction(s) (two dimensional (including imaging modality type) and/or three dimensional) along with what visualization mode(s) and/or portions thereof will be utilized. The system will output a corresponding display based on the user's preferences/selections and/or system defaults.

Figure 11:
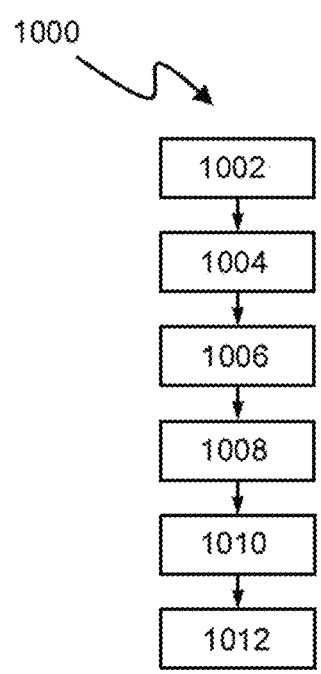
FIG. 11 is a flow diagram of a method for prompting diagnostic action(s) based on obtained physiological data.

FIG. 11 is a flow diagram of a method 1000 of evaluating a vessel system of a patient to recommend a diagnostic procedure for the patient according to an embodiment of the present disclosure. Method 1000 can be implemented by a system described herein, such as system 150 of FIG. 4. As illustrated in FIG. 11, the method 1000 is illustrated as a plurality of enumerated steps or operations. Embodiments of the method 1000 may include additional steps or operations before, after, in between, or as part of the enumerated steps. At step 1002, method 1000 can include obtaining image data from an image of a vessel system. This may be done by contacting networked storage such as an electronic health record storage system to obtain data such as angiogram data. The angiogram data may include a two dimensional angiographic image, a three dimensional angiographic image, and/or a computed tomography angiographic (CTA) image. An example of the angiogram data may be seen in the user interface 500 of FIG. 5 which includes the angiogram 504.

At step 1004, the method 1000 can include obtaining physiology measurements from a vessel of a patient. In one embodiment, a first instrument and a second instrument are positioned within the vessel of the patient while the second instrument is moved longitudinally through the vessel from a first position to a second position. One or more diagnostic measurements (e.g., pressure-based including FFR and iFR, flow-based including CFR, etc.) can be used to gather the physiology measurements to characterize the existence and/or severity of a lesion or lesions within the vasculature of a patient. For example, when FFR is used, areas of a patient's vasculature that have a relatively high FFR (e.g., greater than 0.80) are characterized as not having a lesion or stenosis, while areas with a relatively low FFR (e.g., less than 0.80) are characterized as having a lesion or stenosis. The severity can be evaluated based on the heat map described herein. The physiology measurements may be obtained in a manner that provides at least some location information associated with the measurements.

At step 1006, the method 1000 can include co-registering the physiology measurements with the image data. In this way, the physiological measurements are associated with corresponding portions of the vessel of the patient, producing co-registered physiology measurements. The co-registered physiology measurements can be displayed in an overlaid fashion, such that the physiology measurements may be visualized in association with the angiogram image data. An example may be seen in the user interface 800 of FIGS. 8-10. By co-registering the physiology measurements with the image data, the system 150 may provide additional perspective to a clinician or clinicians. The window 801 may indicate the physical dimensions of the patient's vasculature, which may be sufficient to identify one or more lesions therein, while the physiology measurements indicate the impact or effect of lesions with the vasculature. In some embodiments, co-registering the physiology measurements with the image data may include associating, in a data file, each physiology measurement with a location within the vessel system, identifying a corresponding location for each physiology measurement with the image data, and associating in the co-registered physiology measurements data file, each physiology measurement with its corresponding location within the image of the vessel system. In some embodiments, co-registering the physiology measurements may produce a new data file that includes the co-registered physiology measurements.

At step 1008, the method 1000 can include analyzing the co-registered physiological measurements to identify a region of interest within the vessel system. There are several ways to identify a probable risk area. First, a region of interest may be based on the performance of past medical procedures. For example, if a stent was previously placed in the analysis area, the system 150 may automatically flag the area as a region of interest and recommend further analysis to confirm the accurate placement and functionality of the stent. The placement of the stent may be compared to pre-procedure projections such as a virtual stent to see if expected results have been reached. Second, a region of interest may be based on pressure measurements. As explained in conjunction with FIG. 8, anomalous pressure measurements (such as unusually low FFR readings taken in context with the given vessel anatomy) may automatically prompt a recommendation to take further measurements, conduct another type of diagnostic procedure, or in extreme cases, undertake a medical procedure. Third, regions of interest may be based on anatomical physiological data such as unexpected narrowing of a vessel or the existence of a side branch near a stenosis. Further physiology information that may be considered includes dominance classification, a degree of occlusion of the lesion, a classification of the lesion, a degree of bending of a vessel of the vessel system, a length of the lesion, a degree of calcification of the lesion, etc. The method of analyzing regions of interests based on the anatomical physiology is discussed in conjunction with FIG. 10.

At step 1010, the method 1000 can include formulating a recommendation of a diagnostic or medical procedure based on the analysis of the co-registered physiology measurements. This recommendation includes confirming measurements taken by the system 150, collecting further measurements, running a diagnostic procedure such as iFR measurements, PCI planning or CABG mapping, or performing a medical procedure. The formulation of this recommendation may take into multiple sources of co-registered information and may assign unequal weights to the various sources as necessary. For instance, the recommendation may assign great importance on whether the patient had a previous myocardial infarction and/or previous PCI, especially in the location at issue, while assigning lesser importance to the actual FFR measurement in a vessel. The recommendation may also be based on comparison of current physiological measurements with previously recorded physiological measurements from a database. Other sources of information that form part of the analysis and formulation of the recommendation include patient history such as age, gender, or preexisting conditions such as diabetes or hypertension.

At step 1012, the method 1000 can include displaying the recommendation to a user. In some embodiments, the recommendation is automatically displayed on a user interface 800 such as that shown in FIGS. 8-10. The recommendation may be displayed on the screen of the display or in a separate window such as window 840. In some cases, recommendations are displayed alongside imagery to show the exact region of interest that the recommendation pertains to, as shown in FIG. 10. Furthermore, recommendations may involve multiple procedures as discussed in conjunction with FIG. 5. Recommendation of procedures may be read by medical professionals during the course of a procedure to help guide diagnoses. Additionally, the recommendation may be used as an educational tool. For instance, the recommendation and factors used by the system 150 in the analysis used to formulate the recommendation may be presented to a patient, or the family members or guardian of a patient to help explain the reasoning of the medical professional or the likelihood of future procedures.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for evaluating a vessel of a patient, the system comprising:
    an intravascular catheter or guide wire configured to be positioned within the vessel of the patient; and
    a processor configured for communication with an extravascular imaging system and the intravascular catheter or a guide wire, wherein the processor is configured to:
        receive, from the extravascular imaging system, extravascular image data for the vessel;
        control the intravascular catheter or guide wire to obtain intravascular data of a first modality for the vessel;
        co-register the intravascular data of the first modality with the extravascular image data;
        determine, based on the co-registered intravascular data of the first modality, a region of interest of the vessel;
        generate, based on the co-registered intravascular data of the first modality, a recommendation to obtain intravascular data of a different second modality at the region of interest of the vessel; and
        output, to a display in communication with the processor, a screen display comprising:
            a graphical representation of the vessel based on the extravascular image data;
            a graphical representation of the co-registered intravascular data of the first modality positioned at one or more corresponding first locations in the graphical representation of the vessel; and
            a graphical representation of the recommendation positioned at a second location in the graphical representation of the vessel corresponding to the region of interest.

2. The system of claim 1, wherein the extravascular image data comprises at least one of two-dimensional angiographic image data, three-dimensional angiographic image data, or computed tomography angiographic (CTA) image data.

3. The system of claim 1, wherein the graphical representation of the vessel comprises at least one of an angiographic image or a three-dimensional model of the vessel.

4. The system of claim 1, wherein the intravascular data of the first modality comprises pressure data.

5. The system of claim 4, wherein the graphical representation of the co-registered intravascular data comprises one or more numerical pressure ratios calculated based on the pressure data.

6. The system of claim 4, wherein the graphical representation of the co-registered intravascular data comprises a coloring based on the pressure data and overlaid on the graphical representation of the vessel.

7. The system of claim 1, wherein the processor is configured to generate the recommendation to obtain the intravascular data of the different second modality based on geometric information generated from the extravascular image data.

8. The system of claim 7, wherein the geometric information comprises at least one of a dominance classification, a degree of occlusion of a lesion of the vessel, a classification of the lesion of the vessel, a degree of bending of the vessel, a length of the lesion of the vessel, or a degree of calcification of the lesion of the vessel.

9. The system of claim 1, wherein the processor is configured to automatically determine the region of interest based on the co-registered intravascular data of the first modality.

10. The system of claim 9, wherein the region of interest comprises a first region of interest, and wherein the processor is further configured to:
    automatically determine a second region of interest of the vessel based on the co-registered intravascular data of the first modality;
    generate, based on the co-registered intravascular data of the first modality, a recommendation to obtain intravascular data of a third modality at the second region of interest of the vessel, wherein the third modality is different from the second modality.

11. The system of claim 1, wherein the intravascular data of the second modality comprises intravascular image data.

12. The system of claim 11, wherein the processor is further configured to receive, from an intravascular imaging device different from the intravascular catheter or guide wire, the intravascular image data, and wherein the screen display further comprises a graphical representation of the intravascular image data.

13. The system of claim 11, wherein the processor is further configured to determine a classification a lesion of the vessel based on the intravascular image data, and wherein the screen display further comprises a graphical representation of the classification of the lesion.

14. The system of claim 1, wherein at least one of the one or more first locations is the same as the second location.

15. The system of claim 1, wherein the one or more first locations are different from the second location.

16. The system of claim 1, further comprising the extravascular imaging system.

* * * * *